(12) United States Patent
Kawauchi et al.

(10) Patent No.: US 6,657,069 B2
(45) Date of Patent: Dec. 2, 2003

(54) AMIDO COMPOUNDS AND PROCESS FOR PRODUCING THE SAME

(75) Inventors: Miho Kawauchi, Tsukuba (JP); Noritsugu Yamasaki, Himeji (JP); Mitsuru Ohno, Tsukuba (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/378,726

(22) Filed: Mar. 5, 2003

(65) Prior Publication Data

US 2003/0130519 A1 Jul. 10, 2003

Related U.S. Application Data

(62) Division of application No. 09/799,607, filed on Mar. 7, 2001, now Pat. No. 6,548,674.

(30) Foreign Application Priority Data

Mar. 7, 2000 (JP) ........................................ 2000-062458

(51) Int. Cl.$^7$ ............................................ C07D 207/00
(52) U.S. Cl. ....................................................... 548/541
(58) Field of Search .......................................... 548/541

(56) References Cited

PUBLICATIONS

B. Glatz, et al. "A Total Synthesis and Structural Aspects of Racemic 8–Oxygenated Tetracycline$^{1a,b}$", *Journal of the American Chemical Society*, 1979, pp. 2171–2181.

S.J. Davis, et al. "Heterocyclic Syntheses with Malonyl Chloride", *Journal of the Chemical Society*, 1962, pp. 3553–3561.

*Primary Examiner*—Joseph K. McKane
*Assistant Examiner*—Kamal Saeed
(74) *Attorney, Agent, or Firm*—Birch, Stewart, Kolasch & Birch, LLP

(57) ABSTRACT

A 6-aminocarbonylmethyl-4H-2,3-dioxin-4-one compounds can be produced by reacting a 6-halomethyl-4H-2,3-dioxin-4-one compound with a primary or secondary amine and carbon monoxide. The reaction may be carried out in the presence of a catalyst comprising a platinum group metal. 3-oxopentanedicarboxylic acid monoamides and 3-oxopentanedicarboxylic acid amide esters can be are produced by reacting 6-aminocarbonylmethyl-4H-2,3-dioxin-4-one compound with an alcohol or water. Using such intermediates, 6-aminocarbonylmethyl-4H-2,3-dioxin-4-one compound, 3-oxopentanedicarboxylic acid amide esters can provide in an easy and simple and efficient manner.

1 Claim, No Drawings

AMIDO COMPOUNDS AND PROCESS FOR PRODUCING THE SAME

This application is a divisional of application Ser. No. 09/799,607, filed on Mar. 7, 2001, now U.S. Pat. No. 6,548,674 the entire contents of which are hereby incorporated by reference and for which priority is claimed under 35 U.S.C. §120; and this application claims priority of Application No. 62458/2000 filed in Japan on Mar. 7, 2000 under 35 U.S.C. §119.

FIELD OF THE INVENTION

The present invention relates to an intermediate useful for obtaining 3-oxopentanedicarboxylic acid amide compounds, a process for producing the same, and a process for producing 3-oxopentanedicarboxylic acid amide compounds using the above intermediate. The 3-oxopentanedicarboxylic acid amide compounds is beneficial as intermediates of fine chemicals such as medicinals and agrochemicals and beneficial as raw materials for polyamides.

BACKGROUND OF THE INVENTION 3-oxopentanedicarboxylic acid amide compounds are compounds useful as intermediates of fine chemicals, such as medicinals and agrochemicals, and as raw materials for polyamides.

As a process for synthesizing the compound, for example, Journal of the American Chemical Society, 1979, pages 2171–2181 discloses a process for producing methyl N-t-butyl-3-oxoglutaramate which comprises boiling mixture of dimethyl ester of 3-oxopentanedicarboxylic acid, p-toluenesulfonic acid and dioxane, and adding butylamine to the mixture dropwise for 9 hours. In this process, however, the conversion reaction of the ester into the amide proceeds slowly, and reaction operability is decreased. Moreover, in this process, since an ester amide is produced from a diester, by-products such as diamide tend to form. Thus, it is disadvantageous that the process is applied to an industrial production of an ester amide.

JOURNAL OF THE CHEMICAL SOCIETY, 1962, pages 3553–3561 discloses a process for synthesizing 3-oxopentanedicarboxylic acid amide carboxylic acid (in particular, γ-(benzoylcarbamoyl)acetoacetic acid) which comprises synthesizing chloropyranooxazine from malonyl chloride or pyrone acid chloride and benzonitrile, hydrolyzing chloropyranooxazine to form hydroxypyranooxazine, and treating the resulting oxazine with an acid. This process is, however, disadvantageous in the efficient utilization of the reactants because of by-producing carbon dioxide. Moreover, when various substituents are introduced into 3-oxopentanedicarboxylic acid amide carboxylic acid, the reaction step comes complicated.

SUMMARY OF THE INVENTION

Accordingly, it is an object of the present invention to provide amide compounds useful for producing 3-oxopentanedicarboxylic acid amide compounds in an industrially advantageous manner, a process for producing the same, and a process for producing 3-oxopentanedicarboxylic acid amide compounds using the same.

Another object of the invention is to provide novel 3-oxopentanedicarboxylic acid amide compounds.

As a result of intensive investigations made to solve the above problems, the present inventors found that, by using the specific amide compound, 3-oxopentanedicarboxylic acid amide compounds can be produced efficiently. These findings have now led to completion of the present invention.

Thus, the novel amide compounds of the present invention are represented by the following formula (1):

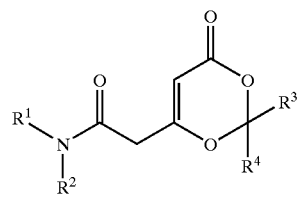

(1)

wherein $R^1$, $R^2$, $R^3$ and $R^4$ are the same or different, each represents a hydrogen atom, an aliphatic hydrocarbon group, an alicyclic hydrocarbon group or an aromatic hydrocarbon group, the hydrocarbon groups may optionally have a substituent, $R^1$ and $R^2$ may form a ring with an adjacent nitrogen atom, and $R^3$ and $R^4$ may form a ring with an adjacent carbon atom.

The amide compound (1) can be produced by reacting a halogen compound represented by the following formula (2) with carbon monoxide and an amine represented by the following formula (3). The reaction is carried out in the presence of a catalyst comprising at least one element selected from the group consisting of Group 8 elements, Group 9 elements and Group 10 elements of the Periodic Table of Elements. In the formula (2), X may be an iodine or bromine atom. A halogen compound of the formula (2) in which X is a fluorine or chlorine atom is reacted with carbon monoxide and the alcohol or water in the presence of at least one member selected from among iodinating agents and brominating agents.

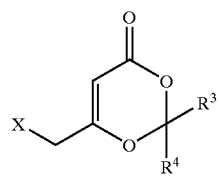

(2)

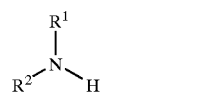

(3)

wherein X is a halogen atom and $R^1$, $R^2$, $R^3$ and $R^4$ have the same meanings as defined above.

According to the present invention, a dicarboxylic acid amide compound represented by the following formula (5) can be produced by reacting the amide compound (1) with an alcohol or water represented by the following formula (4).

$R^5OH$ (4)

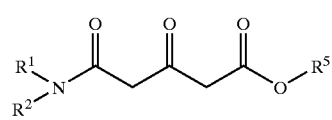

(5)

wherein R represents a hydrogen atom, an aliphatic hydrocarbon group, an alicyclic hydrocarbon group or an aromatic hydrocarbon group, the hydrocarbon groups may optionally have a substituent, and $R^1$ and $R^2$ have the same meaning as defined above.

The present invention also includes a novel dicarboxylic acid amide compound represented by the following formula (5a):

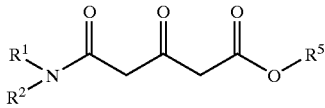

(5a)

wherein $R^1$ represents a hydrogen atom, $R^2$ represents a cycloalkyl group, and $R^5$ represents an alkyl group, the cycloalkyl group and the alkyl group may optionally have a substituent.

DETAILED DESCRIPTION OF THE INVENTION

[Amide Compounds (1)]

Referring to the amide compound represented by the above formula (1), the aliphatic hydrocarbon groups represented by $R^1$, $R^2$, $R^3$ and $R^4$ may be either straight chain or branched chain hydrocarbon groups, and may be either saturated or unsaturated hydrocarbon groups. Examples of the aliphatic hydrocarbon groups include alkyl groups (preferably $C_{1-10}$ alkyl groups, more preferably $C_{1-6}$ alkyl groups, in particular $C_{1-4}$ alkyl groups), such as methyl, ethyl, propyl, isopropyl, butyl, isobutyl and t-butyl groups; alkenyl groups (preferably $C_{2-6}$ alkenyl groups, in particular $C_{2-4}$ alkenyl groups), such as vinyl, allyl, isopropenyl, 1-butenyl and 2-butenyl groups; alkynyl groups (preferably $C_{2-6}$ alkynyl groups, in particular $C_{2-4}$ alkynyl groups), such as ethynyl, propynyl, 1-butynyl and 2-butynyl groups.

The alicyclic hydrocarbon groups may be saturated or unsaturated hydrocarbon groups. Examples of the alicyclic hydrocarbon groups include cycloalkyl groups (e.g., $C_{3-10}$ cycloalkyl groups, preferably $C_{4-8}$ cycloalkyl groups, in particular $C_{4-6}$ cycloalkyl groups), such as cyclopropyl, cyclobutyl, cyclopentyl, cyclohexyl and cyclooctyl groups; cycloalkenyl groups (e.g., $C_{3-10}$ cycloalkenyl groups, preferably $C_{4-8}$ cycloalkenyl groups, in particular $C_{4-6}$ cycloalkenyl groups), such as cyclopropenyl, cyclobutenyl, cyclopentenyl, cyclohexenyl and cyclooctenyl groups; cycloalkynyl groups (e.g., $C_{4-8}$ cycloalkynyl groups, in particular $C_{5-6}$ cycloalkynyl groups), such as cyclopentynyl, cyclohexynyl and cyclooctynyl groups.

Examples of the aromatic hydrocarbon groups include aryl groups (e.g., $C_{6-10}$ aryl groups), such as phenyl and naphthyl groups; aralkyl group groups (e.g., $C_{6-10}$ aryl-$C_{1-4}$ alkyl groups), such as benzyl and phenethyl groups.

The alicyclic hydrocarbon group and the aromatic hydrocarbon group may form a condensed ring with, for example, a heterocycle.

The hydrocarbon groups may have a substituent. As the substituent, there may be mentioned, halogen atoms, such as fluorine, chlorine and bromine atoms; $C_{1-4}$ alkyl groups such as methyl and ethyl groups; acyl groups [e.g. alkylcarbonyl group (e.g., $C_{1-4}$ alkyl-carbonyl groups) such as acetyl group; arylcarbonyl groups (e.g., $C_{6-10}$ aryl-carbonyl groups) such as benzoyl group], acyloxy groups [e.g., alkylcarbonyloxy groups (e.g., $C_{1-4}$ alkyl-carbonyloxy groups) such as acetyloxy group; arylcarbonyloxy groups (e.g., $C_{6-10}$ aryl-carbonyloxy groups) such as benzoyloxy group], alkoxy groups (e.g., $C_{1-4}$ alkoxy groups) such as methoxy and ethoxy groups; alkoxycarbonyl groups ($C_{1-4}$ alkoxy- carbonyl groups) such as methoxycarbonyl group; aryl groups (e.g., $C_{6-10}$ aryl groups) such as phenyl and naphthyl groups; aryloxy groups such as phenoxyl group; heterocyclic groups (e.g., 5- to 8-membered heterocyclic groups such as pyridyl, piridino, piperidyl and piperidino groups).

The ring formed by $R^1$ and $R^2$ together with an adjacent nitrogen atom includes a saturated or unsaturated heterocycle having at least one nitrogen atom as an ring-constituting atom, and may be either an aromatic or non-aromatic ring. As the heterocycles, there may be mentioned, 5- to 8-membered heterocycles (in particular, 5- or 6-membered heterocycles) such as pyrrole, pyrroline, pyrazole, imidazole, pyrrolidine, piperidine, piperazine, pyridine, triazine, carbazole, indole and purine rings. The heterocycles may have oxygen atom and/or sulfur atom as a ring-constituting atom. As the heterocycles, there may be mentioned, heterocycles containing nitrogen atom and oxygen atom such as oxazolidine, oxazolone, oxazine, oxadiazine, oxaziazole, oxatriazole and morpholine rings; heterocycles containing nitrogen atom and sulfur atom such as thiazan, thiazine, thiazolidine, thiazoline, thiazole, thiadiazine, thiadiazoline and thiadiazole rings; heterocycles containing nitrogen, oxygen and sulfur atoms such as oxathiazine ring. The heterocycle is usually a 5-to 8-membered ring, in particular, 5- or 6-membered ring.

The ring formed by $R^3$ and $R^4$ together with an adjacent carbon atom includes alicyclic hydrocarbon rings corresponding to the above-mentioned alicyclic hydrocarbon groups (e.g., $C_{3-10}$ cycloalkanes, $C_{3-10}$ cycloalkenes), aromatic hydrocarbon rings corresponding to the above-mentioned aromatic hydrocarbon groups (e.g., benzene ring) and heterocycles.

Preferred as $R^1$ and $R^2$ are alkyl groups (in particular, $C_{1-6}$ alkyl groups), cycloalkyl groups (e.g., $C_{3-10}$ cycloalkyl groups, in particular $C_{5-8}$ cycloalkyl groups), aryl groups (in particular, $C_{6-10}$ aryl groups) and aralkyl groups (e.g., $C_{6-10}$ aryl-$C_{1-4}$ alkyl groups such as benzyl and phenethyl groups). Preferred as $R^1$ and $R^2$ form a 5- or 6-membered heterocycle together with an adjacent nitrogen atom (e.g., pyrrolidine, piperidine, pyridine rings). $R^3$ and $R^4$ are preferably alkyl groups, more preferably $C_{1-4}$ alkyl group (in particular, $C_{1-2}$ alkyl group).

As such amide compounds (1), there maybe mentioned, among others, 6-N—$C_{1-4}$ alkylaminocarbonylmethyl-2,2-di$C_{1-4}$ alkyl-4H-1,3-dioxin-4-one (e.g. 6-N-methylaminocarbonylmethyl-2,2-dimethyl-4H-1,3-dioxin-4-one, 6-N-ethylaminocarbonylmethyl-2,2-dimethyl-4H-1,3-dioxin-4-one and 6-N-t-butylaminocarbonylmethyl-2,2-dimethyl-4H-1,3-dioxin-4-one; 6-N,N-di$C_{1-4}$ alkylaminocarbonylmethyl-2,2-di$C_{1-4}$ alkyl-4H-1,3-dioxin-4-one (e.g. 6-N,N-dimethylaminocarbonylmethyl-2,2-dimethyl-4H-1,3-dioxin-4-one and 6-N-ethyl-N-methyl-aminocarbonylmethyl-2,2-dimethyl-4H-1,3-dioxin-4-one); 6-N—$C_{6-10}$ arylaminocarbonylmethyl-2,2-di$C_{1-4}$ alkyl-4H-1,3-dioxin-4-one; 6-N—($C_{6-10}$ aryl-$C_{1-4}$ alkyl) aminocarbonylmethyl-2,2-di$C_{1-4}$ alkyl-4H-1,3-dioxin-4-one; 6-(1-pyrrolyl)carbonylmethyl-2,2-dimethyl-4H-1,3-dioxin-4-one, 6-(1-pyrrolinyl)carbonylmethyl-2,2-dimethyl-4H-1,3-dioxin-4-one, 6-(1-pyrrolidinyl)carbonylmethyl-2,2-dimethyl-4H-1,3-dioxin-4-one, 6-piperidinocarbonylmethyl-2,2-dimethyl-4H-1,3-dioxin-4-one, 6-pyridinocarbonylmethyl-2,2-dimethyl-4H-1,3-dioxin-4-one, 6-(1-pyrazolyl)carbonylmethyl-2,2-dimethyl-4H-1,3-dioxin-4-one, 6-(1-indolyl)carbonylmethyl-2,2-dimethyl-4H-1,3-dioxin-4-one, 6-morpholinocarbonylmethyl-2,2-dimethyl-4H-1,3-dioxin-4-one, 6-(7-purinyl)carbonylmethyl-2,2-dimethyl-4H-1,3- dioxin-4-one, 6-(9-carbazolyl)carbonylmethyl-2,2-dimethyl-4H-1,3-dioxin-4-one, 6-(1-imidazolyl)carbonylmethyl-2,2-dimethyl-4H-1,3-dioxin-4-one.

[Process for Producing the Amide Compounds (1)]

The amide compounds (1) can be produced by reacting a halogen compound represented by the above formula (2) with carbon monoxide and an amine represented by the above formula (3). The reaction order of each component is not particularly limited. The reaction of the halogen compound (2) with the amine (3) may be carried out in coexistence of carbon monoxide, and the halogen compound (2) may be reacted with carbon monoxide, followed by reacting with the amine (3).

Referring to the above halogen compound (2), X is, for example, a halogen atom such as a fluorine, chlorine, bromine or iodine atom. Among these halogen atoms, a bromine or iodine atom is preferred.

In cases where X is a fluorine or chlorine atom, to the reaction system for producing the amide compound (1) is added an iodinating agent (e.g., iodine, alkali metal iodides (potassium iodide, sodium iodide, etc.)) or a brominating agent (e.g., bromine, alkali metal bromides (sodium bromide, potassium bromide, etc.)) so that the atom X may be converted into an iodine or bromine atom. When the iodinating or brominating agent is used, an amount of the iodinating or brominating agent may be selected within the wide range of a catalytic amount to an equivalent mole amount relative to the halogen compound (in which X is a chlorine or fluorine atom), and is, for example, about 0.001 to 0.8 mol, preferably about 0.005 to 0.3 mol, more preferably about 0.01 to 0.2 mol, per 1 mol of the halogen compound (in which X is a chlorine or fluorine atom).

Carbon monoxide may be pure carbon monoxide gas, and may be used as a mixed gas with an inert gas (e.g., nitrogen, argon, helium).

The amount of carbon monoxide is not less than 1 mol and is selected from a wide range of, for example, about 1 to 10,000 mol, preferably about 1 to 1,000 mol, more preferably about 1 to 100 mol) per 1 mol of the halogen compound (2). The reaction is usually carried out in a carbon monoxide-containing atmosphere (preferably an atmosphere of carbon monoxide).

In the reaction for producing the amide compound (1), the amount of the amine (3) may be selected, depending on species of amine, a reaction manner, a reaction rate and others, within a wide range of, for example, about 0.1 to 100,000 mol per 1 mol of the halogen compound (2). The amount of the amine (3) is usually about 0.5 to 1,000 mol (e.g., about 0.8 to 100 mol) and preferably about 0.8 to 10 mol per 1 mol of the halogen compound (2).

The reaction with carbon monoxide may be carried out in the presence of a carbonylation catalyst. As such catalyst, a catalyst comprising a Group 8 element of the Periodic Table of Elements (e.g. iron Fe, ruthenium Ru, osmium Os), a Group 9 element (e.g. cobalt Co, rhodium Rh, iridium Ir), a Group 10 element (e.g. nickel Ni, palladium Pd, platinum Pt) and so forth may be used. The catalyst may comprise the element singly or in combination of two or more of them.

Preferred catalyst comprises a platinum group metal. As the platinum group metal, there may be used, Group 8 elements of the Periodic Table of Elements (ruthenium Ru, osmium Os), Group 9 elements (rhodium Rh, iridium Ir), Group 10 elements (palladium Pd, platinum Pt) [J. Dealey: "Inorganic Chemistry", translated into Japanese by H. Hamaguchi and H. Kanno, published by Tokyo Kagaku Dojin (1982), page 360 or elsewhere]. Among these elements, Group 10 elements of the Periodic Table of Elements, in particular Pd are preferred.

The valence of the metal constituting the catalyst is particularly limited and is usually about 0 to 4 valences and preferably about 0 to 2 valences.

The catalyst is usually used as a simple substance, or a compound or complex containing the metal element. As examples of metal-containing compound, there may be mentioned metal salts [e.g., inorganic acid salts such as hydrochloric acid salts, sulfuric acid salts, nitric acid salts, salts with carbonic acid (e.g. carbonates, hydrogen carbonates), salts with phosphoric acid (e.g. phosphates, hydrogen phosphates, dihydrogen phosphates), and boric acid salts; organic acid salts such as carboxylic acid salts (e.g., fatty acid salts such as formates, acetates, lactates, oxalates, naphthenate); thiocyaniate, halides (e.g. chlorides, bromides) and so forth.

As the complex, there may be mentioned a complex resulting from coordination of a ligand to the metal element or the metal-containing compound. As examples of the ligand, there may be mentioned phosphorus compounds such as phosphines (e.g. trialkylphosphines such as tri(n-butyl)phosphine; triarylphosphines such as triphenylphosphine), nitrile, OH (hydroxo), alkoxyl groups (e.g. methoxy and ethoxy groups), acyl groups (e.g. acetyl and propionyl groups), alkoxycarbonyl groups [e.g. methoxycarbonyl (acetato) and ethoxycarbonyl groups], acetylacetonato, cyclopentadienyl group, halogen atoms (e.g., chlorine, bromine), CO, oxygen atom, $H_2O$ (aquo), nitrogen-containing compounds (e.g., $NH_3$(ammine), NO, $NO_2$(nitro), $NO_3$(nitrato), alkylenediamide (e.g., ethylenediamine), pyridine, phenanthroline) and so forth. In the complex or complex salt, the same kind or different kind of ligands may coordinate singly or in combination of two or more of them. The complex can be composed of a suitable combination of the metal or the metal-containing compound with the ligand.

The metal-containing catalyst may be a homogeneous one or a heterogeneous one. The catalyst may be a solid catalyst supporting the catalyst component on a support. As the support, there may be mentioned a porous support such as activated carbon, zeolite, silica (e.g., silica gel), alumina, silica-alumina, bentonite.

These catalysts may be used alone or in combination.

When the catalyst is a palladium-based one, for instance, the catalyst includes, among others, palladium nitrate, palladium chloride, palladium acetate, acetylacetonatopalladium(II), tetraamminepalladium(II) chloride, bis(ethylenediamine)palladium(II) chloride, potassium tetrachloropalladate(II), potassium tetranitropalladate (II), dichloro-bis(trialkylphosphine)palladium(II), dimethyl-bis(triethylphosphine)palladium(II), biscyclopentadienylpalladium(II), tricarbonylcyclopentadienylpalladium(I), dichloro-$\mu$-bis[bis(dimethylphosphino)methane]dipalladium(I), tetrakis(triphenylphosphine)palladium(0), bis(tricyclohexylphosphine)palladium(0), tetrakis(triethylphosphito)palladium(0), carbonyl-tris(triphenylphosphine)palladium(0), bis(cycloocta-1,5-diene)palladium(0) and tris(dibenzylideneacetone)dipalladium(0).

The amount of the catalyst is usually about 0.001 to 1 mol, preferably about 0.01 to 0.5 mol, more preferably, 0.01 to 0.2 mol per 1 mol of the halogen compound (2).

As the reaction progresses, a halic acid is generated in the reaction system. For neutralizing this halic acid, a base may be added to the reaction system. As examples of the base, there may be mentioned inorganic bases, for example alkali metal or alkaline earth metal hydroxides (e.g. sodium hydroxide, potassium hydroxide, magnesium hydroxide, calcium hydroxide), alkali metal or alkaline earth metal carbonates (e.g. sodium carbonate, potassium carbonate, magnesium carbonate, calcium carbonate), alkali metal or alkaline earth metal hydrogencarbonates (e.g. sodium hydrogencarbonate, potassium hydrogencarbonate, magnesium hydrogencarbonate, calcium hydrogencarbonate), alkali metal or alkaline earth metal carboxylates (e.g., sodium acetate, potassium acetate, magnesium acetate, calcium acetate); organic bases such as $triC_{1-4}$ alkylamines (e.g., triethylamine), heterocyclic amine compounds (e.g., heterocyclic tertiary amine such as pyridine), $C_{1-4}$ alkylanilines (e.g. tertiary amines such as N,N-dimethylaniline) and so forth. Incidentally, a hallic acid may be neutralized with an excess of the amine (3) in lieu of these bases. These bases may be used singly or two or more of them may be used in combination.

The reaction may be carried out in the presence or absence of a solvent. The solvent may be any one, without any particular limitation, provided that the progress of the reaction is not inhibited and the reactants are soluble therein. As examples of the solvent, there may be mentioned ketones (e.g., acetone and methyl ethyl ketone), ethers (e.g., 1,4-dioxane, tetrahydrofuran and diethylether), nitrites (e.g., acetonitrile and benzonitrile), sulfoxides (e.g., dimethylsulfoxide), sulfones (e.g., sulfolane), aliphatic hydrocarbons (e.g., pentane, hexane and octane), aromatic hydrocarbons (e.g., benzene and toluene), halogen-containing compounds (e.g., methylene chloride, chloroform, bromoform, chlorobenzene and bromobenzene). The amount of the solvent is not particularly restricted but should be such that the reactants (halogen compound (2) etc.) can be dissolved therein, and may be selected within a range of, for example, about 1 to 1,000 parts by weight per 1 part by weight of the halogen compound (2).

This reaction is usually carried out at about ordinary pressure (or atmospheric pressure) to 500 atmospheres (about 50 MPa), preferably at about ordinary pressure to 100 atmospheres (about 10 MPa), more preferably at about ordinary pressure to 10 atmospheres (about 1 MPa). If necessary, the reaction may be carried out under reduced pressure for apparatus and/or operational reasons.

In the reaction system, the reaction with carbon monoxide may be carried out just by bring carbon monoxide into contact with the other reactants, and may be carried out not only by gas-liquid contacting but also by blowing carbon monoxide into solution through a blowing tube.

The reaction temperature is not particularly restricted as so far as the reaction temperature may be not less than the melting point and not more than the boiling point of the reaction system under a reaction conditions, and is, for example, about −30° C. to 200° C., preferably about −10° C. to 100° C. The reaction efficiently proceeds even under a mild condition of a room temperature (e.g., about 5 to 40° C.).

[Process for Producing the Dicarboxylic Acid Amide Compounds]

According to the present invention, the dicarboxylic acid amide compounds (monoamides of dicarboxylic acid or dicarboxylic acid amide esters) represented by the following formula (5) can be produced by reacting the above amide compound (1) with an alcohol or water represented by the following formula (4).

$R^5OH$ (4)

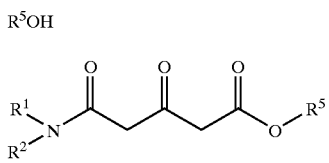

(5)

Wherein $R^5$ represents hydrogen atom, an aliphatic hydrocarbon group, an alicyclic hydrocarbon group or an aromatic hydrocarbon group, these groups may optionally have a substituent. $R^1$ and $R^2$ have the same meanings as defined.

In this reaction, the synthesis method of the amide compound (1) is not particularly limited, and the amide compound (1) may be prepared not only by the above-mentioned process for producing the amide compounds (1) but also by other processes.

In the formulae (4) and (5), as examples of an aliphatic hydrocarbon group, an alicyclic hydrocarbon group, an aromatic hydrocarbon group represented by $R^5$, and of a substituent which these hydrocarbon groups may have, there may be mentioned those groups mentioned hereinabove referring to $R^1$ to $R^4$. Preferred as $R^5$ are a hydrogen atom, $C_{1-10}$ aliphatic hydrocarbon groups (in particular $C_{1-6}$ alkyl groups), $C_{4-8}$ alicyclic hydrocarbon groups and the like. Among these groups, $C_{1-4}$ alkyl groups such as methyl and ethyl groups are preferred.

When $R^1$ and $R^2$ form a ring, it is not necessary for $R^1$ and $R^2$ of the amide compound (2) as a starting material to form a ring, and the ring may form after the preparation of a dicarboxylic acid amide compound (5).

In the reaction for producing a dicarboxylic acid amide compound (5), the amount of alcohol or water (4) may be selected depending on a starting material, a reaction manner and a reaction rate, and is about 0.1 to 100,000 mol, preferably about 0.5 to 1,000 mol, more preferably about 0.8 to 100 mol, per 1 mol of the amide compound (1).

The production reaction of the dicarboxylic acid amide compound (5) can proceed by heating or the other means even in the absence of a catalyst. The reaction may be carried out in the presence of a catalyst to be promoted. As examples of the catalyst, there may be mentioned various acid catalysts, for example, inorganic acids (e.g. sulfuric acid, hydrochloric acid, phosphoric acid, nitric acid), organic acids [carboxylic acid (e.g., $C_{1-10}$ saturated or unsaturated mono- or polycarboxylic acid such as acetic acid and propionic acid), sulfonic acids (e.g., $C_{1-6}$ alkanesulfonic acids such as methanesulfonic acid and ethanesulfonic acid; aromatic sulfonic acids such as benzenesulfonic acid and p-toluenesulfonic acid), halogenated organic acids (e.g., halogenated carboxylic acids such as trifluoroacetic acid; halogenated alkanesulfonic acids such as trifluoromethanesulfonic acid)] and solid acids [sulfuric acid salts (e.g. calcium sulfate), metal oxides (e.g. $SiO_2$, $Al_2O_3$), zeolites (e.g. acidic OH-containing Y, X or A type zeolites), heteropolyacids, ion exchange resins (e.g., cation exchange resins such as H type)]. The catalyst may be used singly or in combination.

The amount of the catalyst is not particularly restricted and is, for example, about 0.001 to 1 mol, preferably about 0.01 to 0.2 mol, per 1 mol of the amide compound (1).

The reaction may be carried out in the presence or absence of a solvent. As a solvent, any of those solvents which can be used in the production of the amide compounds (1) mentioned above can be used. The alcohol or water (4) may be used as a solvent.

This reaction can be carried out usually at ordinary or atmospheric pressure. The reaction may be carried out under reduced pressure or under pressure for reaction conditions, reaction apparatus and/or operational reasons.

The reaction temperature may be usually between the melting point to the boiling point of the reaction system under such reaction conditions as mentioned above and is, for example, about −30° C. to 300° C., preferably about −10° C. to 200° C.

The production of the amide compounds (1) and the dicarboxylic acid amide compounds (5) may be carried out by a conventional method such as batchwise, semi-batchwise and continuous systems.

When the dicarboxylic acid (5) is produced after the amide compound (1) is produced according to the process of the present invention, the amid compound (1) may be isolated or purified and subjected to the production step of the dicarboxylic acid (5), and may be subjected to the production step without isolation or purification.

The amide compounds (1) and the dicarboxylic acid amide compounds (5) can be easily separated and purified respectively by a conventional method such as filtration, concentration, distillation, extraction, ion exchange, electrodialysis, crystallization, recrystallization, adsorption, membrane separation, centrifugation, chromatography (column chromatography, etc.), or a combination means thereof.

[Novel Dicarboxylic Acid Amide Compounds]

According to the process of the present invention, novel dicarboxylic acid amide compounds represented by the following formula (5a) can be produced.

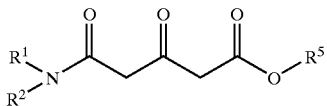
(5a)

wherein $R^1$ represents a hydrogen atom, $R^2$ represents a cycloalkyl group, $R^5$ represents an alkyl group, and the cycloalkyl group and the alkyl group may optionally have a substituent.

As examples of cycloalkyl groups represented by $R^2$, there may be mentioned the cycloalkyl groups mentioned hereinabove referring to $R^1$ to $R^4$ of the formula (1). As examples of alkyl groups represented by $R^5$, there may be mentioned the alkyl groups mentioned hereinabove referring to $R^1$ to $R^4$. As examples of substituents which these groups may have, there may be mentioned various substituents mentioned hereinabove referring to $R^1$ to $R^4$.

Among such dicarboxylic acid amide compounds (5a), as dicarboxylic acid monoamides, there may be mentioned 3-oxopentanedicarboxylic acid N—$C_{5-10}$ cycloalkyl amide such as 3-oxopentanedicarboxylic acid N-cyclohexyl amide. As dicarboxylic acid amide ester, there may be mentioned 3-oxopentanedicarboxylic acid N—$C_{5-10}$ cycloalkyl amide $C_{1-6}$ alkyl ester such as 3-oxopentanedicarboxylic acid N-cyclopentyl amide ethyl ester, 3-oxopentanedicarboxylic acid N-cyclohexyl amide ethyl ester.

Such novel dicarboxylic acid amide compounds can be produced by the above process for producing the dicarboxylic acid amide compounds (5) and is useful as intermediates for fine chemicals such as medicinals and agrochemicals (agricultural chemicals) and as starting materials for polyamides.

According to the present invention, 3-oxopentanedicarboxylic acid amide compound can be efficiently produced since 6-aminocarbonylmethyl-4H-1,3-dioxin-4-ones, which are novel compounds is employed. Moreover, using starting materials relatively easy to obtain and handle, 6-aminocarbonylmethyl-4H-1,3-dioxin-4-ones and further 3-oxopentadicarboxylic acid amide compounds can be produced under a mild condition. Thus, the process of the present invention is broadly used in the various fields and is advantageous for industrial or commercial production.

EXAMPLES

The following examples illustrate the present invention in more detail. They are, however, by no means limitative of the scope of the invention. In the following examples, a methyl group is sometimes abbreviated as Me, an ethyl group as Et, an isopropyl group as i-Pr, a tertiary butyl group as t-Bu, a benzyl group as $PhCH_2$, a cyclohexyl group as c-Hex, tetrahydrofuran as THF.

The IR spectra were recorded on a PERKIN-ELMER 1600 Series FT-IR spectrophotometer.

The NMR spectra were recorded on a BRUKER AM500 spectrometer at 500 MHz ($^1$H-NMR) or 125.7 MHz ($^{13}$C-NMR) with trimethylsilane (TMS) as an internal standard.

The MS spectra were recorded on a Thermoquest LCQ spectrometer using the syringe method and the ionization mode APCI for detecting positive ions.

Example 1

Synthesis of 6-N-benzylaminocarbonylmethyl-2,2-dimethyl-4H-1,3-dioxin-4-one (synthesis from 6-chloromethyl-2,2-dimethyl-4H-1,3-dioxin-4-one A 50-mL two-necked flask was charged with 0.100 g (0.564 mmol) of palladium chloride, 0.782 g (5.66 mmol) of potassium carbonate and 0.940 g (5.66 mmol) of potassium iodide, and a carbon monoxide atmosphere was produced in the system by equipping, in the flask, a balloon (atmospheric pressure) blowing carbon monoxide. To this reaction mixture were added 10 mL of toluene, 0.788 g (7.35 mmol) of benzylamine and 1.0 g (5.66 mmol) of 6-chloromethyl-2,2-dimethyl-4H-1,3-dioxin-4-one, and the mixture was stirred at room temperature for 18 hours in the carbon monoxide atmosphere.

After completion of the reaction, the reaction mixture was filtered and the filtrate obtained was concentrated. To the condensed filtrate were added 50 mL of ethyl acetate and 25 mL of water and the object compound was extracted into an organic phase. The organic phase separated was dried over anhydrous sodium sulfate, filtered and concentrated to give 0.950 g of a dark brown residue.

This residue was subjected to $^1$H-NMR spectroscopy for identification, and as a result, a conversion of the substrate was 68% and 6-N-benzylaminocarbonylmethyl-2,2-dimethyl-4H-1,3-dioxin-4-one (1A) was formed.

The residue was purified by silica gel thin layer chromatography (mobile phase: hexane/ethyl acetate=1/1 (volume ratio)) and 70.0 mg of the compound (1A) was obtained. The Rf value was 0.30. The IR spectrum, NMR spectrum and MS spectrum of the compound (1A) are shown below.

IR (neat): 3312, 2927, 1425, 733 cm$^{-1}$ $^1$H-NMR (CDCl$_3$) ppm: 1.64 (s, 6H, CMe$_2$), 3.17 (s, 2H, CH$_2$CO), 4.44 (d, 2H, J=5.7 Hz, C$_6$H$_5$CH$_2$), 5.40 (s, 1H, CH=C), 7.22–7.35 (m, 5H, C$_6$H$_5$)

$^{13}$C-NMR (CDCl$_3$) ppm: 24.9 (CMe$_2$), 41.5 (CH$_2$CO), 43.8 (CH$_2$NH), 96.1 (HC=), 107.2 (Me$_2$C), 127.6 (C$_6$H$_5$), 127.7 (C$_6$H$_5$), 128.6 (C$_6$H$_5$), 128.7 (C$_6$H$_5$), 137.9 (C$_6$H$_5$), 161.0 (CH$_2$—C=), 165.4 (CONH), 165.9 (=C—CO—O—CMe$_2$-)

CI-MS (m/z): 276 (M$^+$+1, 100%).

Example 2

Synthesis of 6-N-phenylaminocarbonylmethyl-2,2-dimethyl-4H-1,3-dioxin-4-one

The reaction was carried out in the same manner as in Example 1 except that 7.35 mmol of aniline in lieu of benzylamine, and tetrahydrofuran as a solvent in lieu of toluene were employed to give 1.500 g of a residue. This residue was subjected to $^1$H-NMR spectrometry for identification, and as a result, a conversion of the substrate was 100% and 6-N-phenylaminocarbonylmethyl-2,2-dimethyl-4H-1,3-dioxin-4-one (2A) was formed (yield 91%). The NMR spectrum data on this compound (2A) are shown below.

$^1$H-NMR (CDCl$_3$) ppm: 1.73 (s, 6H, CMe$_2$), 3.33 (s, 2H, CH$_2$CO), 5.49 (s, 1H, CH=C), 7.30–7.38 (m, 3H, C$_6$H$_5$), 7.46–7.50 (m, 2H, C$_6$H$_5$).

Example 3
Synthesis of 6-N-cyclohexylaminocarbonylmethyl-2,2-dimethyl-4H-1,3-dioxin-4-one The reaction was carried out in the same manner as in Example 1 except that 7.35 mmol of cyclohexylamine in lieu of benzylamine, and tetrahydrofuran as a solvent in lieu of toluene were employed to give 0.920 g of a residue. This residue was subjected to $^1$H-NMR spectrometry for identification, and as a result, a conversion of the substrate was 100% and 6-N-cyclohexylaminocarbonylmethyl-2,2-dimethyl-4H-1,3-dioxin-4-one (3A) was formed (yield 22%). The NMR spectrum data on this compound (3A) are shown below.

$^1$H-NMR (CDCl$_3$) ppm: 1.09–1.21 (m, 2H, C$_6$H$_{11}$), 1.33–1.43 (m, 2H, C$_6$H$_{11}$), 1.60–1.69 (m, 2H, C$_6$H$_{11}$), 1.70–1.76 (m, 8H, C$_6$H$_{11}$, CMe$_2$), 1.90–1.96 (m, 2H, C$_6$H$_{11}$), 3.12 (s, 2H, CH$_2$CO), 3.75–3.85 (m, 1H, C$_6$H$_{11}$), 5.41 (s, 1H, CH=C).

Example 4
Synthesis of 6-N-t-butylaminocarbonylmethyl-2,2-dimethyl-4H-1,3-dioxin-4-one The reaction was carried out in the same manner as in Example 1 except that 7.35 mmol of t-butylamine in lieu of benzylamine, and tetrahydrofuran as a solvent in lieu of toluene were employed to give 1.670 g of a residue. This residue was subjected to $^1$H-NMR spectrometry for identification, and as a result, a conversion of the substrate was 45% and 6-N-t-butylaminocarbonylmethyl-2,2-dimethyl-4H-1,3-dioxin-4-one (4A) was formed (yield 29%). The NMR spectrum data on this compound (4A) are shown below.

$^1$H-NMR (CDCl$_3$) ppm: 1.36 (s, 9H, t-Bu), 1.71 (s, 6H, CMe$_2$), 3.07 (s, 2H, CH$_2$CO), 5.40 (s, 1H, CH=C).

Example 5
Synthesis of 6-N,N-dimethylaminocarbonylmethyl-2,2-dimethyl-4H-1,3-dioxin-4-one The reaction was carried out in the same manner as in Example 1 except that 7.35 mmol of dimethylamine in lieu of benzylamine, and tetrahydrofuran as a solvent in lieu of toluene were employed to give 0.720 g of a residue. This residue was subjected to $^1$H-NMR spectrometry for identification, and as a result, a conversion of the substrate was 95% and 6-N,N-dimethylaminocarbonylmethyl-2,2-dimethyl-4H-1,3-dioxin-4-one (5A) was formed (yield 38%). The NMR spectrum data on this compound (5A) are shown below.

$^1$H-NMR (CDCl$_3$) ppm: 1.71 (s, 6H, CMe$_2$), 2.30 (s, 6H, Me$_2$NH), 3.03 (s, 2H, CH$_2$CO), 5.46 (s, 1H, CH=C).

Example 6
Synthesis of 6-piperidinoaminocarbonylmethyl-2,2-dimethyl-4H-1,3-dioxin-4-one The reaction was carried out in the same manner as in Example 1 except that 7.35 mmol of piperidine in lieu of benzylamine, and tetrahydrofuran as a solvent in lieu of toluene were employed to give 1.380 g of a residue. This residue was subjected to $^1$H-NMR spectrometry for identification, and as a result, a conversion of the substrate was 100% and 6-piperidinoaminocarbonylmethyl-2,2-dimethyl-4H-1,3-dioxin-4-one(6A) was formed (yield 71%). The NMR spectrum data on this compound (6A) are shown below.

$^1$H-NMR (CDCl$_3$) ppm: 1.41–1.46 (m, 2H, —CH$_2$CH$_2$CH$_2$N—), 1.55–1.62 (m, 4H, —CH$_2$CH$_2$CH$_2$N—), 1.69 (s, 6H, CMe$_2$), 2.41–2.45 (m, 4H, CH$_2$CH$_2$N—), 3.03 (s, 2H, CH$_2$CO), 5.52 (s, 1H, CH=C).

Example 7
Synthesis of 3-oxopentanedicarboxylic acid phenylamide ethyl ester 100 mg (0.399 mmol) of 6-phenylaminocarbonylmethyl-2,2-dimethyl-4H-1,3-dioxin-4-one (7A), 20 mg (0.435 mmol) of ethyl alcohol were dissolved in 5 mL of xylene. The reaction was carried out by heating the mixed solution at a temperature of 140° C. for 6 hours. After the completion of the reaction, the solution was condensed and purified by silica gel thin layer chromatography (mobile phase: hexane/ethyl acetate=1/1 (volume ratio)) to give 20 mg (yield 20%) of the desired compound 3-oxopentanedicarboxylic acid phenylamide ethyl ester (7B). The NMR spectrum data on this compound (7B) are shown below.

$^1$H-NMR (CDCl$_3$) ppm: 1.29 (t, 3H, Et), 3.62 (s, 2H, CH$_2$), 3.72 (s, 2H, CH$_2$), 4.23 (q, 2H, Et), 7.10–7.15 (m, 1H, C$_6$H$_5$), 7.30–7.35 (m, 2H, C$_6$H$_5$), 7.51–7.54 (m, 2H, C$_6$H$_5$)

What is claimed is:

1. A process for producing a dicarboxylic acid amide compound of formula (5):

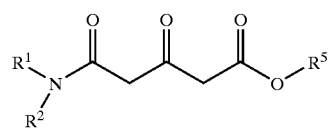

(5)

which comprises reacting an amide of formula (1):

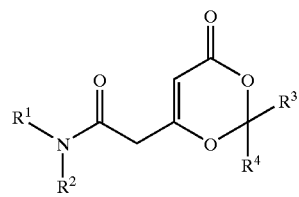

(1)

with an alcohol or water of formula (4):

R$^5$OH     (4)

wherein R$^1$, R$^2$, R$^3$ and R$^4$ are the same or different, each represents a hydrogen atom, an aliphatic hydrocarbon group, an alicyclic hydrocarbon group or an aromatic hydrocarbon group, the hydrocarbon groups may optionally have a substituent, R$^1$ and R$^2$ may form a ring with an adjacent nitrogen atom, and R$^3$ and R$^4$ may form a ring with an adjacent carbon atom wherein R$^5$ represents a hydrogen atom, an aliphatic hydrocarbon group, an alicyclic hydrocarbon group or an aromatic hydrocarbon group, the hydrocarbon groups may optionally have a substituent.

* * * * *